(12) United States Patent
Casey

(10) Patent No.: US 7,534,269 B2
(45) Date of Patent: *May 19, 2009

(54) C-SHAPED DISC PROSTHESIS

(75) Inventor: Niall Casey, Boston, MA (US)

(73) Assignee: DePuy Spine, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/781,688

(22) Filed: Jul. 23, 2007

(65) Prior Publication Data

US 2008/0015703 A1 Jan. 17, 2008

Related U.S. Application Data

(63) Continuation of application No. 10/908,788, filed on May 26, 2005, now Pat. No. 7,261,738.

(60) Provisional application No. 60/584,055, filed on Jun. 30, 2004.

(51) Int. Cl.
A61F 2/44 (2006.01)

(52) U.S. Cl. .................. 623/17.12; 623/17.14

(58) Field of Classification Search .... 623/17.11–17.16
See application file for complete search history.

(56) References Cited

U.S. PATENT DOCUMENTS

| | | | |
|---|---|---|---|
| 4,743,260 A | 5/1988 | Burton | |
| 5,092,866 A | 3/1992 | Breard | |
| 5,282,863 A | 2/1994 | Burton | |
| 5,387,213 A | 2/1995 | Breard et al. | |
| 5,415,661 A | 5/1995 | Holmes | |
| 5,474,086 A | 12/1995 | McCormick et al. | |
| 5,540,688 A | 7/1996 | Navas | |
| 5,556,431 A | 9/1996 | Buttner-Janz | |
| 5,562,737 A | 10/1996 | Graf | |
| 5,571,191 A | 11/1996 | Fitz | |
| 5,672,175 A | 9/1997 | Martin | |
| RE36,221 E | 6/1999 | Breard et al. | |
| 5,961,516 A | 10/1999 | Graf | |
| RE36,758 E | 6/2000 | Fitz | |
| 6,132,464 A | 10/2000 | Martin | |
| 6,267,764 B1 | 7/2001 | Elberg | |
| 6,273,888 B1 | 8/2001 | Justis | |
| 6,387,130 B1 | 5/2002 | Stone et al. | |
| 6,419,703 B1 | 7/2002 | Fallin | |
| 6,554,831 B1 | 4/2003 | Rivard et al. | |
| 6,565,605 B2 | 5/2003 | Goble | |

(Continued)

FOREIGN PATENT DOCUMENTS

DE 3741493 6/1989

(Continued)

Primary Examiner—Bruce E Snow
(74) Attorney, Agent, or Firm—Nutter McClennen & Fish LLP

(57) ABSTRACT

Exemplary implants and methods are provided for stabilizing adjacent vertebrae. In one embodiment, an implant is provided having a shape that allows the implant to be positioned between adjacent vertebrae using a posterior approach while avoiding contact with the spinal cord. For example, the implant can include an anterior portion that is adapted to be positioned between adjacent vertebrae, and a posterior portion that is adapted to extend around a spinal cord. In certain exemplary embodiments, the implant can also be configured to allow motion between the adjacent vertebrae.

16 Claims, 3 Drawing Sheets

U.S. PATENT DOCUMENTS

| | | | |
|---|---|---|---|
| 6,579,319 B2 | 6/2003 | Goble | |
| 6,610,091 B1 | 8/2003 | Reiley | |
| 6,620,196 B1 * | 9/2003 | Trieu | 623/17.16 |
| 6,632,235 B2 * | 10/2003 | Weikel et al. | 606/192 |
| 6,645,207 B2 | 11/2003 | Dixon | |
| 6,656,178 B1 | 12/2003 | Veldhuizen et al. | |
| 6,669,729 B2 | 12/2003 | Chin | |
| 6,811,567 B2 | 11/2004 | Reiley | |
| 7,018,416 B2 * | 3/2006 | Hanson et al. | 623/17.16 |
| 2002/0065557 A1 | 5/2002 | Goble et al. | |
| 2002/0072800 A1 | 6/2002 | Goble et al. | |
| 2002/0123806 A1 | 9/2002 | Reiley | |
| 2002/0133155 A1 | 9/2002 | Ferree | |
| 2003/0004572 A1 | 1/2003 | Goble et al. | |
| 2003/0028250 A1 | 2/2003 | Reiley et al. | |
| 2003/0055427 A1 | 3/2003 | Graf | |
| 2003/0083657 A1 | 5/2003 | Drewry | |
| 2003/0109880 A1 | 6/2003 | Shirado et al. | |
| 2003/0135277 A1 | 7/2003 | Bryan et al. | |
| 2003/0153912 A1 | 8/2003 | Graf | |
| 2003/0171749 A1 | 9/2003 | Le Couedic et al. | |
| 2003/0171750 A1 | 9/2003 | Chin | |
| 2003/0191470 A1 | 10/2003 | Ritland | |
| 2003/0191532 A1 | 10/2003 | Goble et al. | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0006391 A1 | 1/2004 | Reiley | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0111154 A1 | 6/2004 | Reiley | |
| 2004/0116927 A1 | 6/2004 | Graf | |
| 2004/0143264 A1 | 7/2004 | McAfee | |
| 2004/0186475 A1 | 9/2004 | Falahee | |
| 2004/0236329 A1 | 11/2004 | Panjabi | |
| 2005/0033431 A1 | 2/2005 | Gordon et al. | |
| 2005/0033432 A1 | 2/2005 | Gordon et al. | |
| 2005/0033439 A1 | 2/2005 | Gordon et al. | |
| 2005/0101954 A1 | 5/2005 | Simonson | |
| 2005/0101956 A1 | 5/2005 | Simonson | |
| 2005/0113927 A1 | 5/2005 | Malek | |
| 2005/0171609 A1 * | 8/2005 | Humphreys et al. | 623/17.15 |

FOREIGN PATENT DOCUMENTS

| | | |
|---|---|---|
| EP | 0669109 | 2/1994 |
| GB | 2207607 | 2/1989 |
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | WO-2004/024011 | 3/2004 |
| WO | WO-2004/034916 | 4/2004 |
| WO | 2005/032432 | 4/2005 |
| WO | 2005/067824 | 7/2005 |

* cited by examiner

C-SHAPED DISC PROSTHESIS

CROSS-REFERENCE TO RELATED APPLICATIONS

The present application is a continuation of U.S. patent application Ser. No. 10/908,788 filed on May 26, 2005 and entitled "C-Shaped Disc Prosthesis," which claims priority to U.S. Provisional Application Ser. No. 60/584,055, filed on Jun. 30, 2004 and entitled "C-Disc." These references are hereby incorporated by reference in their entireties.

FIELD OF THE INVENTION

The present invention relates to spinal implants and methods.

BACKGROUND OF THE INVENTION

Disease, advancing age, and trauma can lead to changes in various bones, discs, joints, and ligaments of the body. Some changes and trauma often manifest themselves in the form of damage or degeneration to a spinal disc. This condition often results in chronic back pain, which can be anywhere from mild to severe. This pain can sometimes be eliminated by spinal fusion in which two adjacent vertebral bodies are jointed together after removing the intervening intervertebral disc. A prosthetic device is usually placed between the two adjacent vertebral bodies, in place of the removed disc, to fill the space left by the removed disc and to allow bone to grow between the two vertebral bodies.

More recently, spinal implants have been developed that allow motion between the adjacent vertebrae, thereby restoring normal function to the vertebrae. While these implants have been met with great success, they typically require an anterior surgical approach to be used to position the implant between adjacent vertebrae so as to avoid contact with the spinal cord. Most anterior surgical approaches, however, tend to be more invasive than posterior approaches due to the nature and amount of the anatomy that needs to be displaced in order to successfully access the disc space.

Accordingly, there remains a need for improved methods and devices for replacing a spinal disc, and in particular to methods and devices that use a posterior surgical approach.

SUMMARY OF THE INVENTION

The present invention provides various spinal implants and methods for stabilizing the spine. In one exemplary embodiment, a spinal disc prosthesis is provided having an anterior portion that is adapted to be positioned between adjacent vertebrae, and a posterior portion that is adapted to extend around a spinal cord. In certain exemplary embodiments, the implant can be substantially C-shaped.

While the implant can have a variety of configurations, in one exemplary embodiment the anterior portion of the implant can be adapted to allow adjacent vertebrae to articulate relative to one another. For example, the anterior portion of the implant can include first and second domed surfaces formed thereon. Alternatively, or in addition, the anterior portion of the implant can be formed from a compressible material or can include a compressible member to allow movement between the adjacent vertebrae.

In another exemplary embodiment, the anterior portion of the implant can include opposed arms having a central member disposed therebetween. The central member can have a variety of configurations. For example, it can be formed from or can include a compressible material, or it can be in the form of an inflatable member. The central member can be separate from the opposed arms, or it can be fixedly or movably coupled to the opposed arms using a variety of techniques. For example, in one exemplary embodiment at least one of the opposed arms can include an opening formed therein for seating a portion of the central member. The central member can include wings extending from opposed sides thereof, and the opposed arms of the anterior portion of the implant can include openings formed therein for receiving the wings.

Exemplary methods for replacing a spinal disc between adjacent vertebrae are also provided. In one exemplary embodiment, the method can include removing a spinal disc disposed between adjacent vertebrae, and positioning a posterior portion of an implant around a spinal cord and positioning an anterior portion of the implant between the adjacent vertebrae. The implant can be configured to allow movement of the adjacent vertebrae. In an exemplary embodiment, the implant is positioned between the adjacent vertebrae using a posterior surgical approach.

In another exemplary embodiment, the method can include positioning a central member between the adjacent vertebrae. In certain embodiments, the central member can be positioned between the adjacent vertebrae prior to positioning the implant, and the anterior portion of the implant can be positioned around the central member. In other embodiments, the method can include inflating a central member positioned between opposed arms of the anterior portion of the implant.

In yet another exemplary embodiment, a method for stabilizing adjacent vertebrae is provided and includes positioning a central member between adjacent vertebrae, positioning a posterior portion of an implant around a spinal cord, and positioning opposed arms of an anterior portion of the implant on opposed lateral sides of the central member. In one exemplary embodiment, the opposed arms of the anterior portion of the implant can be positioned on opposed lateral sides of the central member by sliding the opposed arms around the central member such that wing members extending from opposed lateral sides of the central member are received within openings formed in the opposed arms. In another exemplary embodiment, the central member can be implanted using a posterio-lateral approach, and the implant can be implanted using a posterior approach.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various methods and devices for repairing or replacing damaged, injured, diseased, or otherwise unhealthy intervertebral discs. In one exemplary embodiment, an implant is provided having a shape that allows the implant to be positioned between adjacent vertebrae using a posterior approach while avoiding contact with the spinal cord. In certain exemplary embodiments, the implant can also be configured to allow motion between the adjacent vertebrae.

Figure 1A:
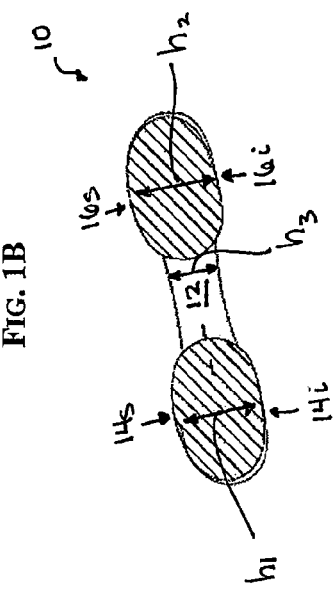
FIG. 1A is a superior perspective view of one exemplary embodiment of a C-shaped implant.
Figure 1B:
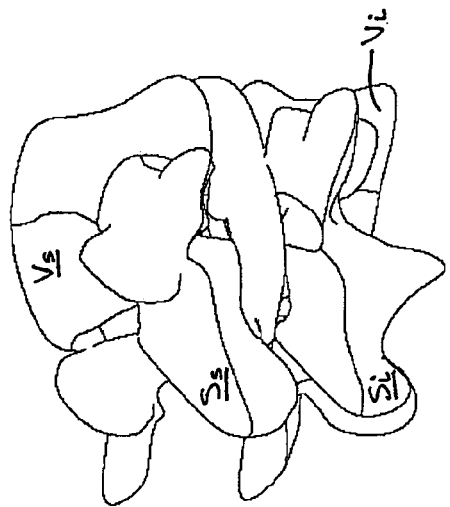
FIG. 1B is a cross-sectional view of the C-shaped implant shown in FIG. 1A taken across line B-B.

FIGS. 1A and 1B illustrate one exemplary embodiment of a spinal implant 10 having a substantially U-shaped or C-shaped unitary configuration. In particular, the implant 10 includes a posterior portion 12a that is adapted to be positioned around a patient's spinal cord to allow for a posterior surgical approach, and an anterior portion 12b that is adapted to be disposed between adjacent vertebrae. A person skilled in the art will appreciate that the terms "U-shaped" or "C-shaped" are intended to include any implant 10 having a generally or partially curved structure with an opening in one side thereof. Further, these terms are intended to include any implant that has an open anterior portion and a posterior portion that can be disposed around a spinal cord, and an anterior portion that can be disposed between adjacent vertebrae. The shape and configuration of the implant 100 is not intended to be limited to only a U- or C-shaped configuration.

The posterior portion 12a of the implant 10 can have a variety of shapes and sizes, but in the illustrated exemplary embodiment the posterior portion 12a is in the form of a U-shaped, C-shaped, or semi-circular member having a relatively large central opening 18a formed therein. Such a shape allows the posterior portion 12a to be positioned around the spinal cord in a patient's spinal column. The posterior portion 12a can also have a relatively low profile, so as to allow the posterior portion 12a to be positioned between the spinous processes of adjacent vertebrae. A person skilled in the art will appreciate that the posterior portion 12a can have a variety of other shapes, and that the shape can be adapted based on the intended use. For example, in the illustrated exemplary embodiment the facets of the adjacent vertebrae are preferably removed to allow the posterior portion 12a to be positioned around the spinal cord. However, the posterior portion 12a of the implant 10 could be shaped to allow the facets on the adjacent vertebrae to remain intact and optionally to articulate relative thereto.

The anterior portion 12b of the implant 10 can also have a variety of shapes and sizes, but in the illustrated exemplary embodiment the anterior portion 12b of the implant 10 includes opposed arms 14, 16 that extend from the posterior portion 12a in a substantially parallel arrangement, and that define an opening 18b therebetween. The opening 18b between the arms 14, 16 can be smaller than the opening 18a at the posterior portion 12a of the implant 10, but it is preferably large enough to allow the spinal cord to pass therethrough when the implant 10 is being implanted. While the shape and size of each arm 14, 16 can vary, in one exemplary embodiment each arm 14, 16 is in the form of a lobe that extends from the posterior portion 12a, and that has a height $h_1$, $h_2$ that is greater than a height $h_3$ of the posterior portion 12a, and a width $w_1$, $w_2$ that is greater than a width $w_3$ of the posterior portion 12a of the implant 10. Such a configuration allows the arms 14, 16 to occupy additional space between the adjacent vertebrae, thereby providing sufficient support for the vertebrae.

The opposed arms 14, 16 can also include a variety of other features that can vary depending on the intended use and desired result once implanted. For example, in one exemplary embodiment each arm 14, 16 can have a shape that is adapted to allow the adjacent vertebrae to articulate relative thereto. For example, as shown in FIG. 1B, each arm 14, 16 includes domed superior and inferior surfaces $14s$, $16s$, $14i$, $16i$. The domed surfaces $14s$, $16s$, $14i$, $16i$ can be formed on any portion of each arm 14, 16, but in an exemplary embodiment the domed surfaces $14s$, $16s$, $14i$, $16i$ are formed along the anterior portion of the implant 10 adjacent to the terminal end of each arm 14, 16. As a result, when the arms 14, 16 are positioned between adjacent vertebrae, the domed surfaces $14s$, $16s$, $14i$, $16i$ will be substantially centrally located relative to the adjacent vertebrae, thereby allowing the vertebrae to articulate relative thereto. While domed surfaces $14s$, $16s$, $14i$, $16i$ are shown, the arms 14, 16 can have a variety of other configurations to allow articulation of adjacent vertebrae. For example, each arm 14, 16 can include a ball or other member movably disposed therein.

In another exemplary embodiment, each arm 14, 16 can be configured to absorb shock between the adjacent vertebrae. For example, the arms 14, 16, or a portion of the arms 14, 16, can be compressible. This can be achieved by forming the arms 14, 16 from a compressible material, embedding a compressible material in the arms 14, 16, or by coupling a compressible material to a portion of the arms 14, 16. The arms 14, 16 can thus be formed from a single unitary component, or they can be formed from separate components that are coupled to one another and to the posterior portion 12a. Suitable compressible materials include, by way of non-limiting example, biocompatible polymers and metals.

The implant 10 can also include features to facilitate engagement of the adjacent vertebrae. In an exemplary embodiment, where engagement features are included, at least a portion of the implant 10 is preferably compressible to allow movement between the adjacent vertebrae. Techniques for mating the implant 10 to adjacent vertebrae include, by way of non-limiting example, surface features, such as teeth, that engage the endplates of the vertebrae, surface coatings or materials that allow bone growth into the implant 10 to occur, or other materials or features that will engage the adjacent vertebrae.

Figure 1C:
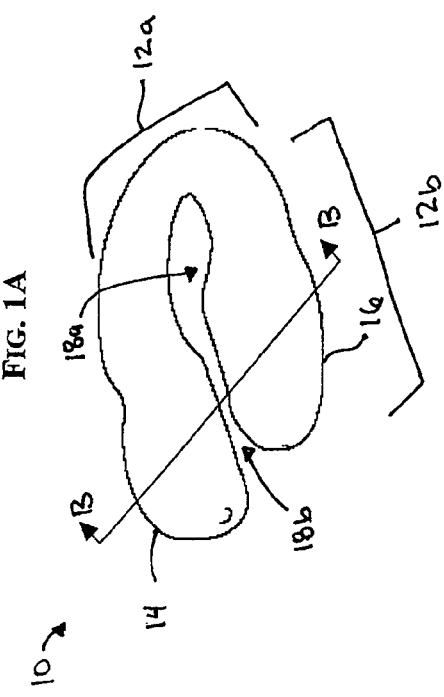
FIG. 1C is a superior perspective view of the C-shaped implant shown in FIG. 1A implanted between adjacent vertebrae, showing only the inferior vertebra.
Figure 1D:
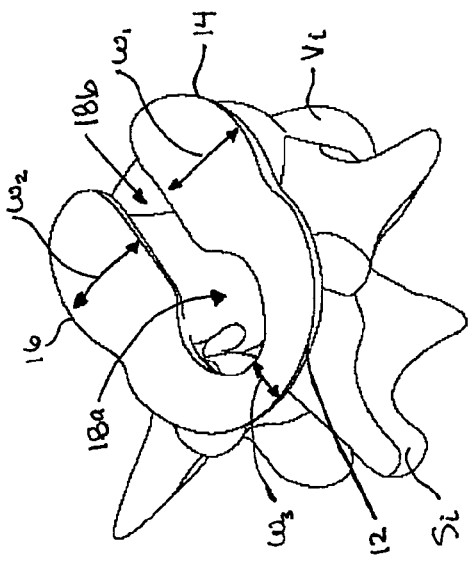
FIG. 1D is a posterior perspective view of the C-shaped implant shown in FIG. 1A implanted between adjacent vertebrae.

FIGS. 1C and 1D illustrate the implant 10 in use implant between adjacent vertebrae $V_s$, $V_i$ (FIG. 1C only illustrates the inferior vertebra $V_i$). In an exemplary embodiment, the spinal column is accessed using a posterior surgical approach (which can include posterio-lateral approaches). Once the spinal column is accessed, and prior to positioning the implant 10 between adjacent superior and inferior vertebrae $V_s$, $V_i$, standard surgical techniques can be used to remove the natural disc disposed between the adjacent vertebrae $V_s$, $V_i$, and preferably to remove the facet joints between the adjacent vertebrae $V_s$, $V_i$. While not shown or described, facet replacement implants can be used in combination with implant 10 to restore function or otherwise replace the removed facet joints.

Once the disc and facets are removed and the adjacent vertebrae are prepared, the implant 10 can be guided between the adjacent vertebrae $V_s$, $V_i$ by passing the spinal cord between the opposed arms 14, 16 and into the central opening 18a. A spinal distractor or other devices known in the art can be used to distract the adjacent vertebrae $V_s$, $V_i$ and guide the implant 10 therebetween. Alternatively, the implant 10 can have a shape that is adapted to distract the vertebrae $V_s$, $V_i$ as the implant 10 is inserted therebetween. Once implanted, as shown, the opposed arms 14, 16 are positioned between the adjacent vertebrae $V_s$, $V_i$, and the posterior portion 12a of the implant is positioned around the spinal cord and between the spinous processes $S_s$, $S_i$ of the adjacent vertebrae $V_s$, $V_i$. The adjacent vertebrae $V_s$, $V_i$ can articulate relative to the implant 10.

Figure 2A:
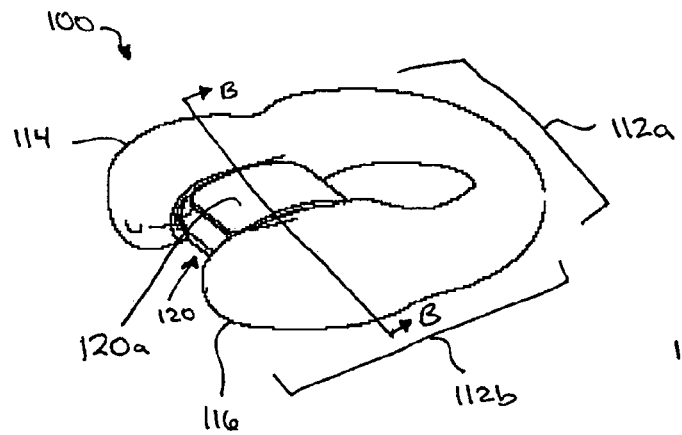
FIG. 2A is a superior perspective view of another exemplary embodiment of a C-shaped implant having a central member.
Figure 2B:
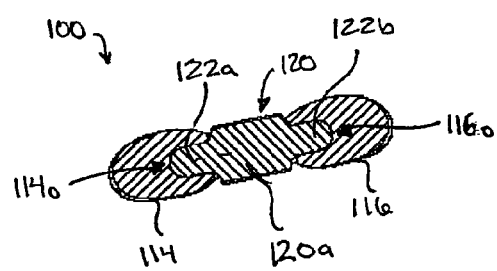
FIG. 2B is a cross-sectional view of an anterior portion of the C-shaped implant shown in FIG. 2A taken across line B-B.
Figure 2C:
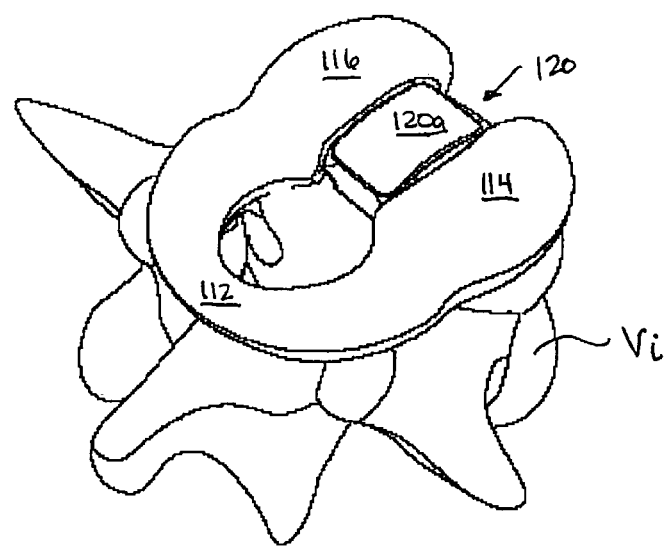
FIG. 2C is a superior perspective view of the C-shaped implant shown in FIG. 2A implanted between adjacent vertebrae, showing only the inferior vertebra.

In another exemplary embodiment, the spinal implant can include a core or central member disposed between the opposed arms of the implant. FIGS. 2A-2C illustrate one exemplary embodiment of an implant 100 having a posterior portion 112a, an anterior portion 112b with opposed arms 114, 116, and a central member 120 disposed between the opposed arms 114, 116. While the central member 120 can have a variety of shapes and sizes, in the illustrated embodiment the central member 120 has a substantially rectangular portion 120a that extends between the opposed arms 114, 116, and opposed wing-members 122a, 122b extending from opposed sides of the rectangular portion 120a. The wing members 122a, 122b can extend into opposed openings 114o, 116, formed on the inwardly facing surfaces of the opposed arms 114, 116, as shown in FIG. 2B, to couple the central member 120 to the arms 114, 116. The openings $114_o$, $116_o$ can be sized to provide a compression or interference fit with the wing members 122a, 122b, thereby providing a substantially rigid connection between the central member 120 and the arms 114, 116. The central member 120 can, however, be formed form a flexible material to allow movement between the central member 120 and the arms 114, 116, if desired. Alternatively, the openings $114_o$, $116_o$ can each have a size that is greater than a size of the wing members 122a, 122b to allow some movement between the central member 120 and the arms 114, 116. A movable configuration is particularly advantageous as it allows each arm 114, 116 to move with relative movement of the adjacent vertebrae. The central member 120 can also be adapted to move relative to the adjacent vertebrae. For example, the central member 120 can include domed or curved superior and inferior surfaces to allow the adjacent vertebrae to articulate relative thereto. Alternatively, the central member 120 can be adapted to fixedly couple to the adjacent vertebrae. As previously described, techniques such as surface features, bone growth materials, etc., can be used to provide a rigid connection with the vertebrae.

Figure 3A:
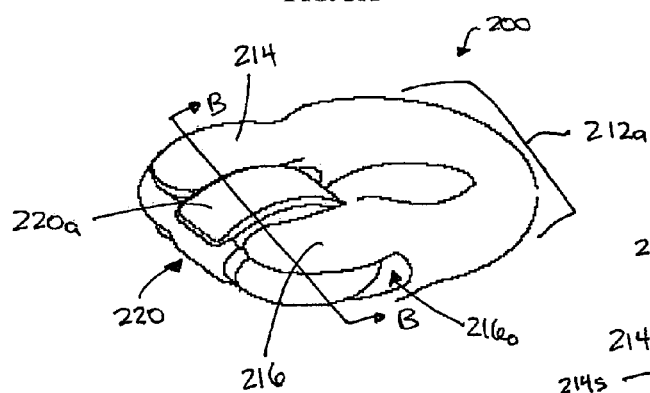
FIG. 3A is a perspective view of yet another exemplary embodiment of a C-shaped implant having a central member.
Figure 3B:
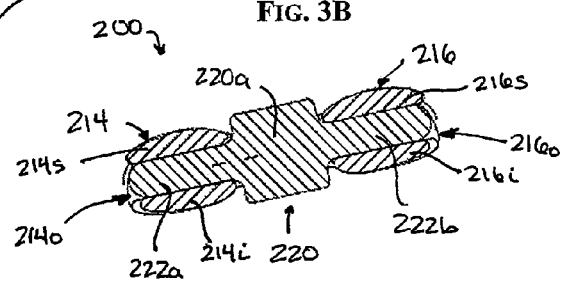
FIG. 3B is a cross-sectional view of an anterior portion of the C-shaped implant shown in FIG. 3A taken across line B-B.
Figure 3C:
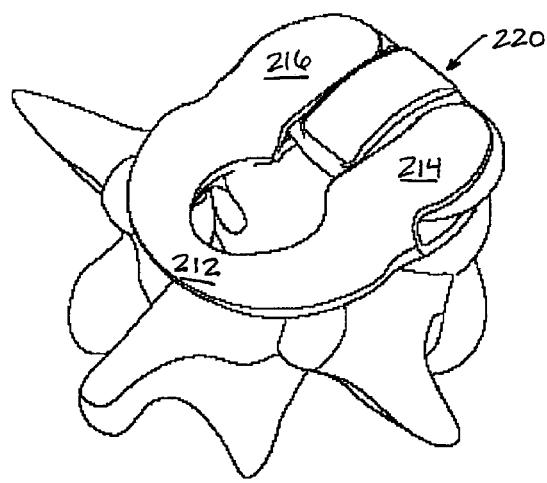
FIG. 3C is a superior perspective view of the C-shaped implant shown in FIG. 3A implanted between adjacent vertebrae, showing only the inferior vertebra.

FIGS. 3A-3C illustrate another exemplary embodiment of an implant 200 having a central member 220 disposed between opposed arms 214, 216 of the anterior portion 212b of the implant 200. The central member 220 is similar to the central member 120 shown in FIGS. 2A-2C, and includes a rectangular portion 220a with wing members 222a, 222b extending from opposed sides thereof. In this embodiment, the wing members 222a, 222b are adapted to be disposed within openings 214o, 216o that extend entirely through each arm 214, 216. As a result, each arm 214, 216 is separated into a superior portion 214s, 216s and an inferior portion 214i, 216i. Such a configuration can allow the superior and inferior portions 214s, 216s, 214i, 216i of each arm 214, 216 to move relative to one another. For example, the central member 220, or at least some or all of the wing members 222a, 222b, can be formed from a compressible material. Thus, when the adjacent vertebrae move relative to one another, the superior and inferior portions 214s, 216s, 214i, 216i of the arms 214, 216 can move to compress the wing members 222a, 222b therebetween. The compressible wing members 222a, 222b are also particularly advantageous as they can be effective to absorb shock.

A person skilled in the art will appreciate that the implant can include a central member having a variety of other shapes, sizes, and configurations, and the particular configuration of the central member can vary depending on the intended use. By way of non-limiting example, the central member can be in the form of a ball, a disc, or other member that has a shape that allows the adjacent vertebrae to articulate relative thereto. The central member can also include multiple pieces. For example, the central member can include a superior endplate member and an inferior endplate member with a movable core disposed therebetween.

The central member can also be formed from a variety of materials. For example, in one exemplary embodiment the central member can be formed from a rigid material, such as a biocompatible plastic or metal. Alternatively, the central member, or a portion of the central member, can be formed from or include a flexible and/or compressible material to allow the central member to flex and/or to be compressed between the adjacent vertebrae. In another exemplary embodiment, the central member can be inflatable such that it can be implanted in a deflated state, and then inflated to restore height and/or occupy the disc space between the adjacent vertebrae. Where an inflatable central member is used, the central member can be separate from the C-shaped implant, or it can be coupled to one or both arms of the implant. In use, the inflatable central member can be inflated prior to positioning the implant between adjacent vertebrae, or after the implant is positioned between the adjacent vertebrae. A person skilled in the art will appreciate that the central member can have a variety of other configurations.

In use, a variety of surgical techniques can be used to position an implant having a core or central member between adjacent vertebrae, and the particular procedure can vary depending on the configuration of the central member. Referring to FIG. 2C, in one embodiment the central member 120 can be inflatable. With the central member 120 in a deflated state, the implant 100 can be positioned between adjacent vertebrae using a posterior approach as previously described with respect to FIGS. 1C and 1D. Once properly positioned between the adjacent vertebrae, an inflation medium, such as air or fluid, e.g., saline, can be introduced into the central member 120 to inflate the central member 120. As a result, the central member 120 will extend between the opposed arms 114, 116 to couple to the arms 114, 116. The inflation medium can optionally be adapted to harden to form a rigid central member 120.

Alternatively, continuing to refer to FIG. 2C, the central member 120 can be pre-disposed between the adjacent vertebrae and the C-shaped portion of the implant 100 can be introduced around the central member 120. Where such a technique is used, the opposed arms 114, 116 are preferably flexible to allow the arms 114, 116 to flex around the wing members 122a, 122b of the central member 120 until the wing members 122a, 112b are positioned within the openings $114_o$, $116_o$ in the arms 114, 116.

In another exemplary embodiment, referring to FIG. 3C, the central member 220 of the implant 200 can be positioned between the adjacent vertebrae using an anterior or posteriolateral surgical approach. The C-shaped portion of the implant 100 can then be guided between the vertebrae, using a posterior approach, by passing the spinal cord between the opposed arms 114, 116, and then sliding the opposed arms 114, 116 around the central member 220. Alternatively, as discussed above, the central member 220 can be inflatable, and it can be pre-positioned between the adjacent vertebrae or inflated after the implant 220 is implanted. A person skilled in the art will appreciate that a variety of other techniques can be used to position the implants disclosed herein between adjacent vertebrae.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal disc prosthesis, comprising:
an anterior portion that includes opposed arms adapted to be positioned between adjacent vertebrae and an inflatable central member disposed between the opposed arms, and a posterior portion that extends between and connects the opposed arms, the posterior portion being adapted to extend around a spinal cord when the anterior portion is positioned between adjacent vertebrae.

2. The implant of claim 1, wherein the anterior portion and the posterior portion having a substantially C-shaped unitary configuration.

3. The implant of claim 1, wherein the opposed arms include domed surfaces formed thereon.

4. The implant of claim 1, wherein the central member is movably disposed between the opposed arms.

5. The implant of claim 1, wherein the central member is formed from a compressible material.

6. The implant of claim 1, wherein at least one of the opposed arms includes an opening formed therein for seating a portion of the central member.

7. The implant of claim 1, wherein the central member includes wings extending from opposed sides thereof, and wherein the opposed arms of the anterior portion include openings formed therein for receiving the wings.

8. A method for implanting a spinal disc prosthesis, comprising:
removing a disc disposed between adjacent vertebrae to prepare a disc space;
introducing opposed arms of a substantially C-shaped implant into the disc space such that a spinal cord passes between the opposed arms and into a central opening of the C-shaped implant; and
positioning the opposed arms between the adjacent vertebrae such that a posterior portion of the implant is positioned around the spinal cord and between the spinous processes of the adjacent vertebrae.

9. The method of claim 8, wherein the implant is introduced between the adjacent vertebrae using a posterior surgical approach.

10. The method of claim 8, wherein the opposed arms allow articulation of the adjacent vertebrae relative thereto.

11. The method of claim 10, wherein the opposed arms include domed surfaces for allowing articulation of the adjacent vertebrae relative thereto.

12. The method of claim 8, further comprising positioning a central member between the opposed arms of the implant.

13. The method of claim 12, further comprising inflating the central member.

14. The method of claim 12, wherein the central member is positioned between the adjacent vertebrae prior to introducing the opposed arms.

15. The method of claim 14, wherein the opposed arms are slid around the central member such that wing members extending from opposed lateral sides of the central member are received within openings formed in the opposed arms.

16. The method of claim 14, wherein the central member is implanted using an posterio-lateral approach, and the implant is implanted using a posterior approach.

* * * * *